United States Patent
Kang et al.

(10) Patent No.: US 9,514,280 B2
(45) Date of Patent: Dec. 6, 2016

(54) METHOD AND APPARATUS FOR CREATING MODEL OF PATIENT SPECIFIED TARGET ORGAN BASED ON BLOOD VESSEL STRUCTURE

(71) Applicant: SAMSUNG ELECTRONICS CO., LTD., Suwon-si (KR)

(72) Inventors: Na Hyup Kang, Seoul (KR); Hyong Euk Lee, Suwon-si (KR); Sang Wook Kim, Seoul (KR); Ji Yeon Kim, Hwaseong-si (KR); Kyung Hwan Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 332 days.

(21) Appl. No.: 13/897,818

(22) Filed: May 20, 2013

(65) Prior Publication Data

US 2014/0032197 A1   Jan. 30, 2014

(30) Foreign Application Priority Data

Jul. 27, 2012   (KR) .................. 10-2012-0082545

(51) Int. Cl.
G06F 19/12   (2011.01)
G06F 19/00   (2011.01)

(52) U.S. Cl.
CPC ........... G06F 19/3437 (2013.01); G06F 19/12 (2013.01)

(58) Field of Classification Search
None
See application file for complete search history.

(56) References Cited

U.S. PATENT DOCUMENTS

| | | | |
|---|---|---|---|
| 7,239,992 B2 | 7/2007 | Ayache et al. | |
| 7,751,984 B2 | 7/2010 | Tang | |
| 7,756,308 B2 * | 7/2010 | Viswanathan | ................ 382/128 |
| 2005/0203385 A1* | 9/2005 | Sundar | ................. G06T 7/0028 |
| | | | 600/427 |
| 2008/0262814 A1 | 10/2008 | Zheng et al. | |
| 2011/0001761 A1* | 1/2011 | Sakuragi | ....................... 345/634 |
| 2011/0060576 A1* | 3/2011 | Sharma et al. | ................. 703/11 |
| 2011/0255761 A1* | 10/2011 | O'Dell et al. | ................ 382/131 |
| 2012/0083696 A1 | 4/2012 | Kitamura | |

FOREIGN PATENT DOCUMENTS

| | | |
|---|---|---|
| JP | 10-127623 | 5/1998 |
| JP | 2003-15877 | 5/2003 |
| JP | 2003-144412 | 5/2003 |
| JP | 2007-125179 | 5/2007 |

(Continued)

*Primary Examiner* — Kee M Tung
*Assistant Examiner* — Nicholas R Wilson
(74) *Attorney, Agent, or Firm* — NSIP Law

(57) ABSTRACT

A method of creating a model of an organ, includes creating a shape model, including a blood vessel structure, of the organ based on three-dimensional (3D) images of the organ, and compartmentalizing the shape model into areas based on an influence of a blood vessel tree with respect to a deformation of the shape model, the blood vessel tree indicating the blood vessel structure. The method further includes deforming the blood vessel structure of the shape model to fit a blood vessel structure of a two-dimensional (2D) image of the organ, and creating the model of the organ based on the deformed blood vessel structure and the areas.

21 Claims, 9 Drawing Sheets

(56) References Cited

FOREIGN PATENT DOCUMENTS

| | | |
|---|---|---|
| JP | 2009-226043 | 10/2009 |
| JP | 2011-224275 | 11/2011 |
| KR | 1019990030339 A | 4/1999 |
| KR | 1020090127091 A | 12/2009 |
| KR | 1020090127100 A | 12/2009 |
| KR | 1020090127101 A | 12/2009 |
| KR | 1020110013738 A | 2/2011 |
| KR | 1020120000722 A | 1/2012 |

* cited by examiner

METHOD AND APPARATUS FOR CREATING MODEL OF PATIENT SPECIFIED TARGET ORGAN BASED ON BLOOD VESSEL STRUCTURE

CROSS-REFERENCE TO RELATED APPLICATIONS

This application claims the benefit under 35 USC 119(a) of Korean Patent Application No. 10-2012-0082545, filed on Jul. 27, 2012, in the Korean Intellectual Property Office, the entire disclosure of which is incorporated herein by reference for all purposes.

BACKGROUND

1. Field

The following description relates to a method and an apparatus for creating a model of a patient specified target organ based on a blood vessel structure.

2. Description of Related Art

Human organs may include a non-rigid deformation characteristic. In more detail, shapes of cardiothoracic and abdominal organs, for example, a liver, a heart, and lungs, may be deformed due to external stimulus applied in breathing and performing laparotomy. Accordingly, modeling of an organ deformation may be performed by navigating inside of a patient in various medical fields, such as, for example, clinical surgery, a preoperative plan, a surgery simulation, and actual surgery. The organ deformation may exhibit distinguishing characteristics for each patient. Accordingly, technology of modeling a patient specified organ deformation may be important.

However, in an actual clinical environment, surgery may be performed based on low quality medical images captured from medical imaging devices during run time. Accordingly, without tracking an organ deformation during run time, it may be difficult to appropriately perform a treatment process and make a clinical determination.

SUMMARY

In one general aspect, there is provided a method of a method of creating a model of an organ, the method including creating a shape model, including a blood vessel structure, of the organ based on three-dimensional (3D) images of the organ, and compartmentalizing the shape model into areas based on an influence of a blood vessel tree with respect to a deformation of the shape model, the blood vessel tree indicating the blood vessel structure. The method further includes deforming the blood vessel structure of the shape model to fit a blood vessel structure of a two-dimensional (2D) image of the organ, and creating the model of the organ based on the deformed blood vessel structure and the areas.

In another general aspect, there is provided an apparatus an apparatus that creates a model of an organ, the apparatus including a creating module configured to create a shape model, including a blood vessel structure, of an organ based on three-dimensional (3D) images of the organ, and a compartmentalizing module configured to compartmentalize the shape model into areas based on an influence of a blood vessel tree with respect to a deformation of the shape model, the blood vessel tree indicating the blood vessel structure. The apparatus further includes a deforming module configured to deform the blood vessel structure of the shape model to fit a blood vessel structure of a two-dimensional (2D) image of the organ, and a run-time creating module configured to create the model of the organ based on the deformed blood vessel structure and the areas.

Other features and aspects will be apparent from the following detailed description, the drawings, and the claims.

DETAILED DESCRIPTION

Figure 1:
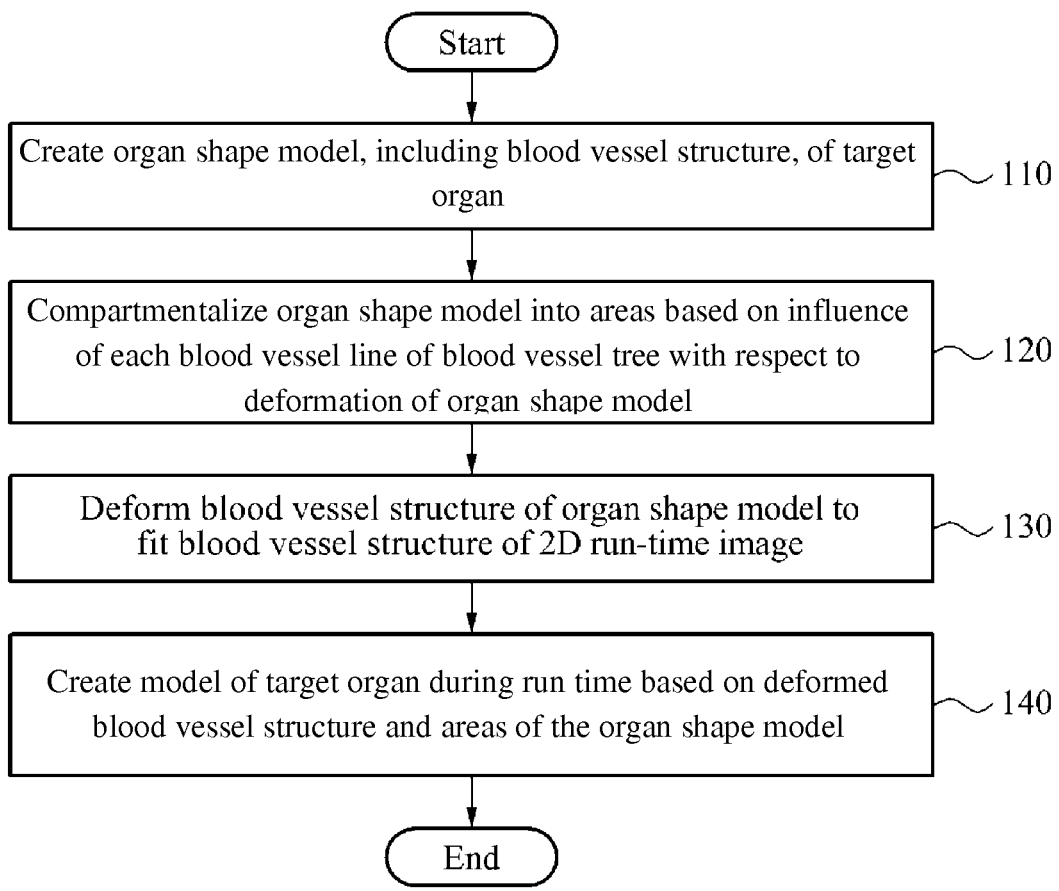
FIG. 1 is a flowchart illustrating an example of a method of creating a model of a target organ.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a flowchart illustrating an example of a method of creating a model of a target organ. Referring to FIG. 1, in operation 110, an apparatus that creates the model of the target organ (hereinafter, a creating apparatus) creates an organ shape model, including a blood vessel structure, of the target organ specified for a patient based on at least two three-dimensional (3D) images of the target organ. Each of the at least two 3D images may be a medical image of a phase for the target organ, such as, for example, a full inhalation and a full exhalation.

In operation 120, the creating apparatus compartmentalizes the organ shape model into areas based on an influence of each blood vessel line of a blood vessel tree with respect to a deformation of the organ shape model. The blood vessel tree indicates the blood vessel structure of the target organ. Operations 110 and 120 may correspond to a preprocessing process preoperatively-performed before a surgery.

In operation 130, the creating apparatus deforms the blood vessel structure of the organ shape model to fit a blood vessel structure of a two-dimensional (2D) run-time image (e.g., an 2D ultrasound (US) medical image) for the target organ.

In operation 140, the creating apparatus creates the model of the target organ during a run time based on the deformed blood vessel structure and the areas of the organ shape model. Operations 130 and 140 may correspond to a run-time process performed during the surgery. In this example, the creating apparatus may deform the blood vessel structure of the organ shape model based on the blood vessel structure of the 2D run-time image, to monitor the target organ during the run time.

Figure 2:
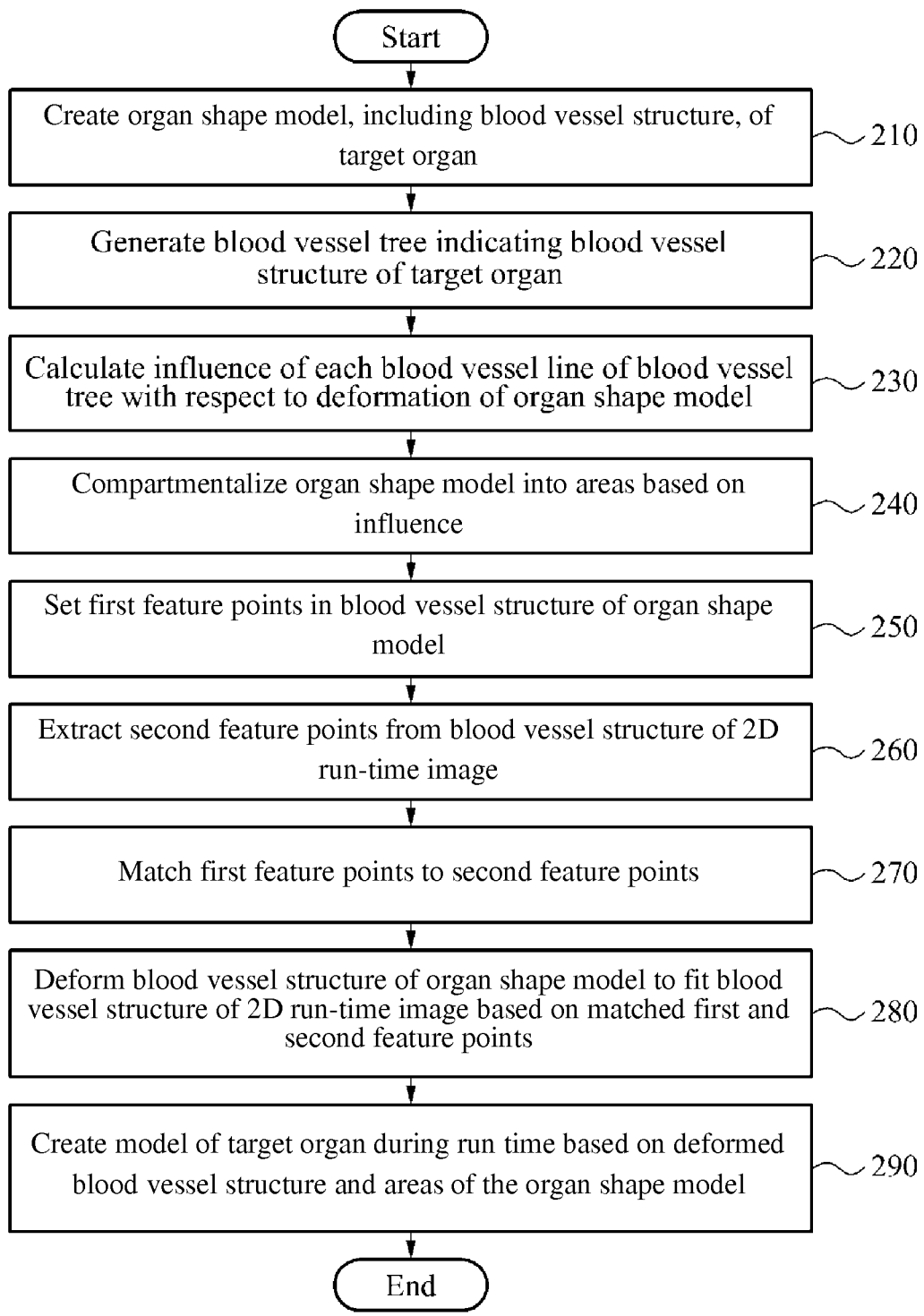
FIG. 2 is a flowchart illustrating another example of a method of creating a model of a target organ.

FIG. 2 is a flowchart illustrating another example of a method of creating a model of a target organ. Referring to FIG. 2, in operation 210, an apparatus that creates the model of the target organ (hereinafter, a creating apparatus) creates an organ shape model, including a blood vessel structure, of the target organ specified for a patient based on at least two 3D images of respective phases for the target organ.

For example, the creating apparatus may mask and thereby segment an area, including the target organ, a blood vessel of the target organ, and/or a tumor, in each of the at least two 3D images. The creating apparatus may further create at least two organ shape models of the respective phases for the target organ based on the segmented area in each of the 3D images. A method of segmenting a target organ will be further described with reference to FIG. 3. A method of creating the organ shape models of respective phases for a target organ will be further described with reference to FIG. 4.

In operation 220, the creating apparatus generates a blood vessel tree indicating the blood vessel structure of the target organ. A method of generating a blood vessel tree will be further described with reference to FIG. 6.

In operation 230, the creating apparatus calculates an influence of each blood vessel line of the blood vessel tree with respect to a deformation of the organ shape model. For example, the creating apparatus may calculate the influence of each blood vessel line of the blood vessel tree with respect to the deformation of the organ shape model based on a minimum distance function or a maximum potential function.

In operation 240, the creating apparatus compartmentalizes the organ shape model into the areas based on the influence of each blood vessel line of the blood vessel tree with respect to the deformation of the organ shape model. For example, the creating apparatus may compartmentalize the organ shape model into the areas based on each blood vessel line including the largest influence with respect to a deformation of a corresponding area of the organ shape model, among blood vessel lines of the blood vessel tree.

Thus, it is possible to reduce an amount of calculations used for a deformation of the entire target organ by enabling the deformation of the entire target organ to be influenced by the blood vessel structure. A method of calculating an influence of each blood vessel line of a blood vessel tree with respect to a deformation of an organ shape model, and a method of compartmentalizing the organ shape model into areas based on the influence, will be further described with reference to FIG. 7.

The creating apparatus deforms the blood vessel structure of the organ shape model to fit a blood vessel structure of a 2D run-time image for the target organ based on one or more first feature points set in the blood vessel structure of the organ shape model and matched to one or more second feature points extracted from the blood vessel structure of the 2D run-time image, as described herein. Without using feature points of an entire area of the target organ, the entire target organ may be deformed based on a predetermined number of the matched feature points in the blood vessel structures.

In operation 250, the creating apparatus sets the first feature points in the blood vessel structure of the organ shape model. A method of setting the first feature points will be further described with reference to FIG. 8. Operations 210 through 250 may correspond to a preprocessing process.

In operation 260, the creating apparatus extracts the second feature points from the blood vessel structure of the 2D run-time image. A method of extracting the second feature points will be further described with reference to FIG. 9.

In operation 270, the creating apparatus matches the first feature points to the second feature points. During the matching of the first and second feature points, the creating apparatus may verify an actually-deformed position of a surface mesh or a center line for the blood vessel structure of the organ shape model.

In operation 280, the creating apparatus deforms the blood vessel structure of the organ shape model to fit the blood vessel structure of the 2D run-time image based on the matched first and second feature points. For example, the creating apparatus may optimize positions of vertices in the organ shape model to satisfy positions of matched vertices in the 2D run-time image, as expressed by the following example of Equation 1. The positions of the vertices for the organ shape model may be an interpolated shape of the surface mesh for the blood vessel structure of the organ shape model, and are set as the first feature points.

$$\min \|F(x)\| + \|G(x)\| \qquad (1)$$

In Equation 1, F(x) denotes a shape difference calculating function in order to enable a new mesh shape x and an existing mesh shape to be similar to each other, and may be a summation of distance differences between vertices. G(x) denotes a summation of distance differences between two vertices at which a feature point of the new mesh shape x matches a vertex of the existing mesh shape.

In operation 290, the creating apparatus creates the model of the target organ during a run time based on the deformed blood vessel structure and the areas of the organ shape model. Operations 260 through 290 may correspond to a run-time process.

For example, the creating apparatus may perform a skeletal subspace deformation method to deform the organ shape model based on, e.g., the blood vessel tree, the areas, and/or the deformed blood vessel structure, of the organ shape model. The creating apparatus may overcome constraints found in the 2D run-time image by matching the first feature points to the second feature points, and may provide the model of the target organ during the run time.

Figure 3:
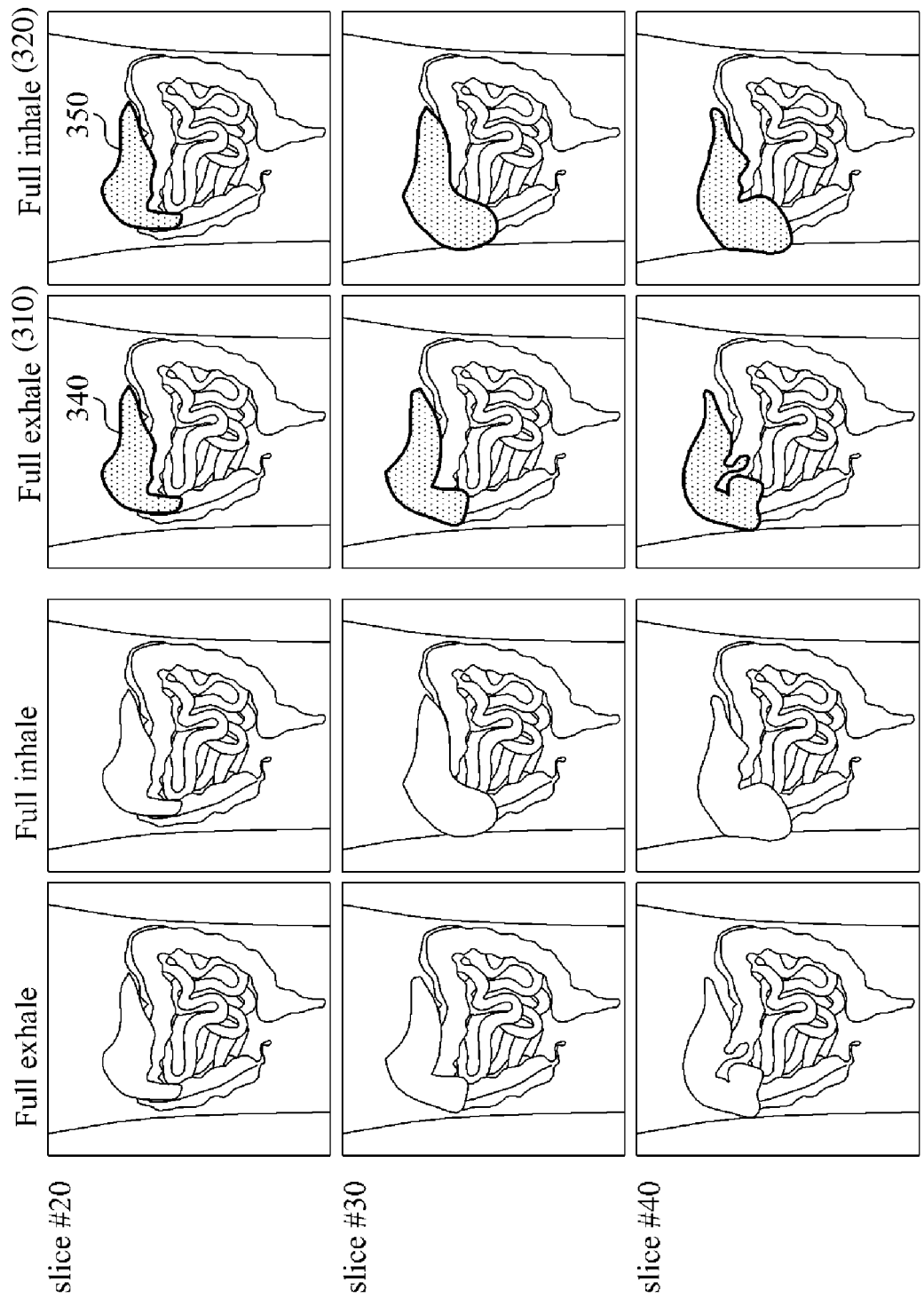
FIG. 3 is a diagram illustrating an example of a method of segmenting a target organ in a method of creating a model of the target organ.

FIG. 3 is a diagram illustrating an example of a method of segmenting a target organ in a method of creating a model of the target organ. Referring to FIG. 3, a creating apparatus acquires a 3D image of the target organ specified for a patient. The 3D image may be a medical image, for example, a magnetic resonance imaging (MRI) image and a computed tomography (CT) image, in which an entire shape of the target organ is included. The 3D image may be of any phase of the target organ, such as, for example, an inhalation, regular breathing, and an exhalation.

Medical images of respective phases for the target organ may be heterogeneous images, for example, an MRI image captured between inhalations and a CT image captured between exhalations, and may be homogeneous images, for example, an MRI image captured between inhalations and an MRI image captured between exhalations. The method of creating the model of the target organ may include a model-based deformation scheme, and thus, may use heterogeneous medical images as well as homogeneous medical images.

A number of medical images for respective phases of the target organ may differ based on a type of the target organ. For example, if an operational characteristic of the target organ, such as a liver and lungs, may be sufficiently-verified by operations performed in an inhalation and an exhalation, a motion of the target organ may be sufficiently-verified based on two medical images captured in an inhalation and an exhalation, respectively. However, if the target organ is a heart, a minimum of four medical images may be needed to verify a process in which blood is flowing through a left atrium, a right atrium, a left ventricle, and a right ventricle. Accordingly, the creating apparatus may acquire the minimum of four medical images needed to verify a deformation characteristic or an operational characteristic of the target organ.

Referring to FIG. 3, the creating apparatus acquires the minimum of four medical images of the target organ in each of slices #20, #30, and #40. Each of the medical images corresponds to a phase of the target organ, namely, a full exhale or a full inhale. The creating apparatus segments an area of the target organ, for example, a liver, in medical images in which a variety of organs are included. For example, the creating apparatus masks areas 340 and 350 of the target organ in a medical image 310 captured in the full exhale, and a medical image 320 captured in the full inhale, respectively.

Masking the area of the target organ decreases a region of interest (ROI). The method of segmenting the area of the target organ may correspond to a preprocessing process, and may be performed through a manual operation of a user, instead of being performed by the creating apparatus. The area of the target organ may be masked in a solid form that includes one or more blood vessels and/or at least one tumor within the target organ. By masking the area of the target organ when segmenting the area of the target area, it is possible to prevent the medical image from being penetrated.

Figure 4:
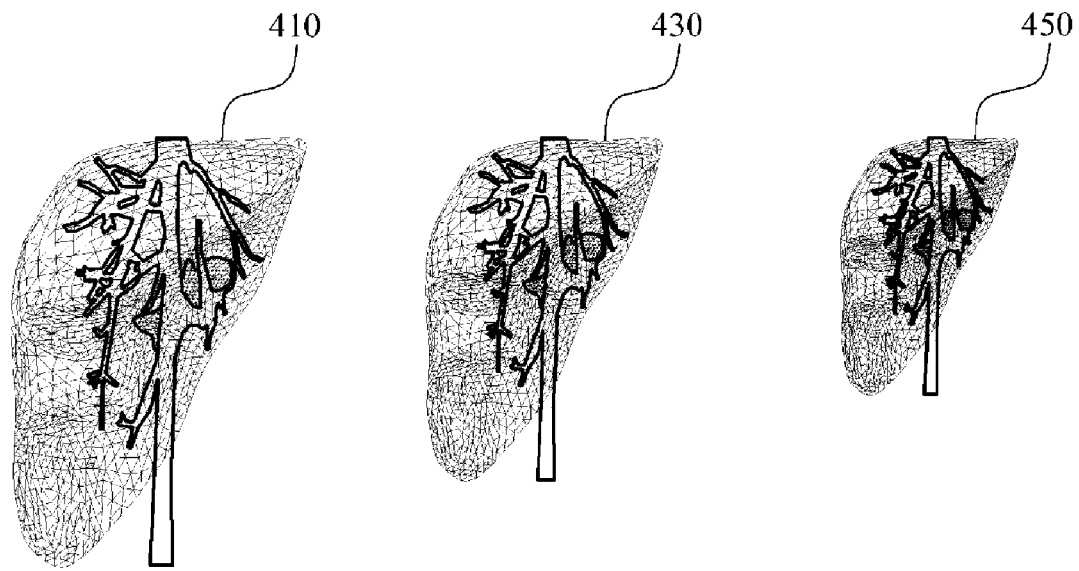
FIG. 4 is a diagram illustrating an example of a method of creating organ shape models of respective phases for a target organ in a method of creating a model of the target organ.

FIG. 4 is a diagram illustrating an example of a method of creating organ shape models of respective phases for a target organ in a method of creating a model of the target organ. Referring to FIG. 4, a creating apparatus creates an organ shape model 410 of the target organ specified for a patient, for example, a liver, at a full inhalation, an organ shape model 430 of the target organ at normal breathing, and an organ shape model 450 of the target organ at a full exhalation.

The method of creating the organ shape models of respective phases for the target organ may correspond to a pre-processing process preoperatively-performed before a surgery. Each of the organ shape models may be created in a form of a 3D mesh model based on a marching cube method. The creating apparatus may generate a deformation matrix between at least two of the organ shape models for the target organ based on at least two 3D images of the target organ, as described herein.

Figure 5:
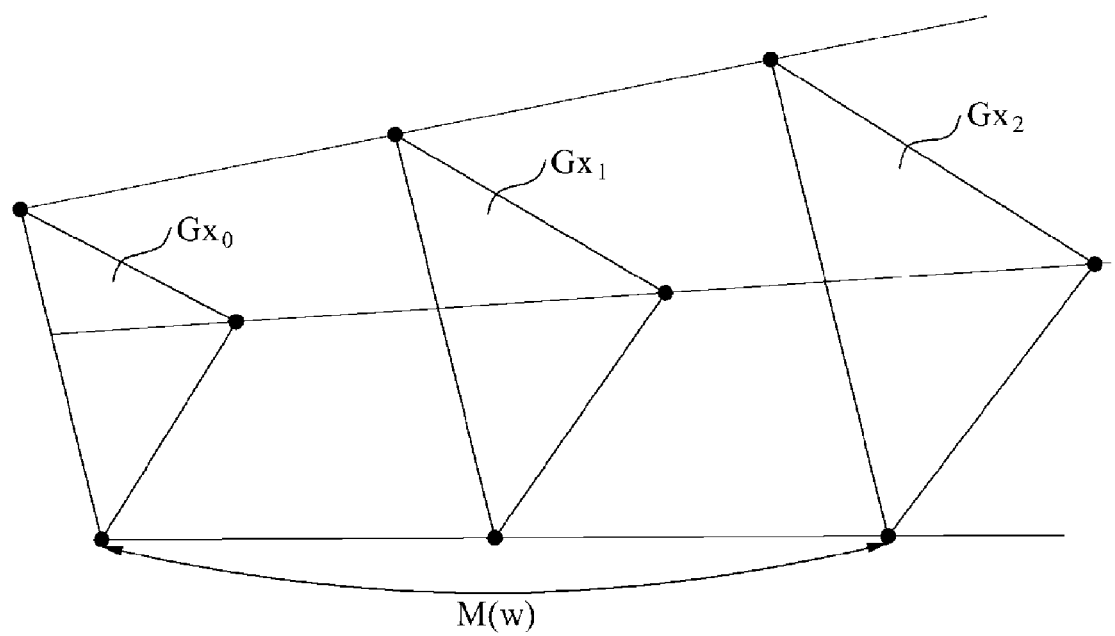
FIG. 5 is a diagram illustrating an example of a deformation space including organ shape models of respective phases for a target organ in a method of creating a model of the target organ.

FIG. 5 is a diagram illustrating an example of a deformation space including organ shape models of respective phases for a target organ in a method of creating a model of the target organ. Referring to FIG. 5, the creating apparatus creates organ shape models $Gx_0$, $Gx_1$, and $Gx_2$ of the respective phases for the target organ of a patient based on three respective 3D images of the target organ. The creating apparatus further calculates a deformation matrix G that defines a deformation space M(w) including the organ shape models $Gx_0$, $Gx_1$, and $Gx_2$.

In this example, the deformation matrix G further indicates a deformation gradient f when a vertex position relationship is given. A relationship between the deformation matrix G and the deformation gradient f may be expressed by the following example of Equation 2:

$$f = Gx \qquad (2)$$

In Equation 2, the deformation gradient f denotes a vector in which elements of a deformation gradient matrix $T_{ij}$ (see Equation 3) defined for each tetrahedron are aligned in a line. Since the deformation gradient matrix $T_{ij}$ is a 3×3 matrix, the deformation gradient f may include a size of 9t×1. Also, x denotes a new vertex position in a 3v form, v denotes a number of vertices, and t denotes a number of tetrahedrons on a tetrahedral mesh. The deformation matrix G may be in a form of, for example, 9t×3v.

The deformation space reflects information about a deformation of the target organ. Therefore, even though only limited information about the deformation of the target organ is provided, it is possible to create the model of the target organ by maintaining a deformation characteristic of the target organ.

The deformation gradient matrix $T_{ij}$ may be decomposed into a rotation component $R_{ij}$ and a stretching component $S_{ij}$ through a polar decomposition as shown in the following example of Equation 3:

$$T_{ij} = R_{ij} S_{ij} \qquad (3)$$

Linear interpolation of the stretching component $S_{ij}$ and nonlinear interpolation of the rotation component $R_{ij}$ may be performed using a matrix exponential function and a logarithm, which is expressed by the following example of Equation 4:

$$T_j(w) = \exp\left(\sum_{i=1}^{l} w_i \log(R_{ij})\right) \cdot \sum_{i=1}^{l} w_i S_{ij} \qquad (4)$$

In Equation 4, $T_j(w)$ denotes a $j^{th}$ tetrahedron of a tetrahedral mesh to be newly generated, $w_i$ denotes a weight of an $i^{th}$ tetrahedral mesh, and l denotes a total number of tetrahedral meshes.

In more detail, Equation 4 may be utilized to interpolate the deformation gradient matrix $T_{ij}$ decomposed through the polar decomposition of Equation 3. A final interpolated deformation gradient matrix may be generated by performing the nonlinear interpolation of the rotation component $R_{ij}$ using a matrix logarithm, by performing the linear interpolation of the stretching component $S_{ij}$, and by recombining the nonlinear-interpolated rotation component $R_{ij}$ and the linear-interpolated stretching component $S_{ij}$.

For example, hereinafter, description will be made based on an example in which a liver is the target organ. However, examples are not limited thereto.

Most organs include a characteristic of consistently maintaining volume in terms of shape deformation. The above characteristic is referred to as "volume maintainability". The volume maintainability may be due to the fact that 70% of cell composition materials include water. Accordingly, in terms of shape deformation of an organ, a shape of the organ may vary with respect to each of an inhalation and an exhalation, whereas a total sum of volumes may be consistently maintained.

Referring to FIG. 5, a shape of the liver is minimized at a start point $x_0$ of an inhalation, and the shape of liver is maximized at a start point $x_2$ of an exhalation. Accordingly, $Gx_0$ indicates the organ shape model in which the shape of liver is minimized, and $Gx_2$ indicates the organ shape model in which the shape of liver is maximized. A shape deformation of the liver is present within the deformation space $M(w)$ between the organ shape models $Gx_0$ and $Gx_2$.

In the inhalation and the exhalation, at least two organ shape models may be created based on the shape of the liver. The deformation space $M(w)$ of the shape of the liver may be defined based on the created at least two organ shape models.

The deformation space $M(w)$ indicates a space in which the organ shape models of the target organ are deformable, and is defined by the deformation matrix G. Predetermined deformation of an organ may be maintained by defining a deformation space of a data-based shape of the organ and by including an organ deformation result in the deformation space. Even if a small number of feature points or noise present in a medical image becomes an issue, robust deformation may be performed since the personalized deformation space is capable of compensating for deformation information with respect to portions in which information is absent.

The volume maintainability may be utilized for a nonlinear system by adjusting a determinant D of a stretching component S of the deformation gradient matrix $T_{ij}$ calculated based on Equation 3. For example, if D=|S| by calculating the determinant D of the linear interpolated stretching component S, the determinant D may be changed to become "1" by changing the stretching component S to be $S'=1/D^{(1/3)}S$.

The determinant D of the deformation gradient matrix $T_{ij}$ indicates a change in a volume of a tetrahedron occurring during a deformation. For example, if D=1, it may indicate that the volume of the tetrahedron is maintained, if D>1, it may indicate that the volume of the tetrahedron increases, and if D<1, it may indicate that the volume of the tetrahedron decreases.

In theory, when the polar decomposition of the deformation gradient matrix $T_{ij}$ is performed, a volume of the rotation component $R_{ij}$ does not vary. Accordingly, when a value of the determinant of the stretching component $S_{ij}$ is forced to become "1" by changing the stretching component $S_{ij}$, a volume of each tetrahedron may be maintained, leading to the entire volume maintainability.

In addition, due to, for example, a matching error, each of tetraheronds that constitute a tetrahedral mesh model may include a different volume. Accordingly, a method of initially calculating the determinant of the stretching component $S_{ij}$, obtaining an interpolation value based on the input weight $w_i$ of the tetrahedral mesh, and resealing the determinant of the final stretching component based on the interpolation value, may be utilized.

Figure 6:
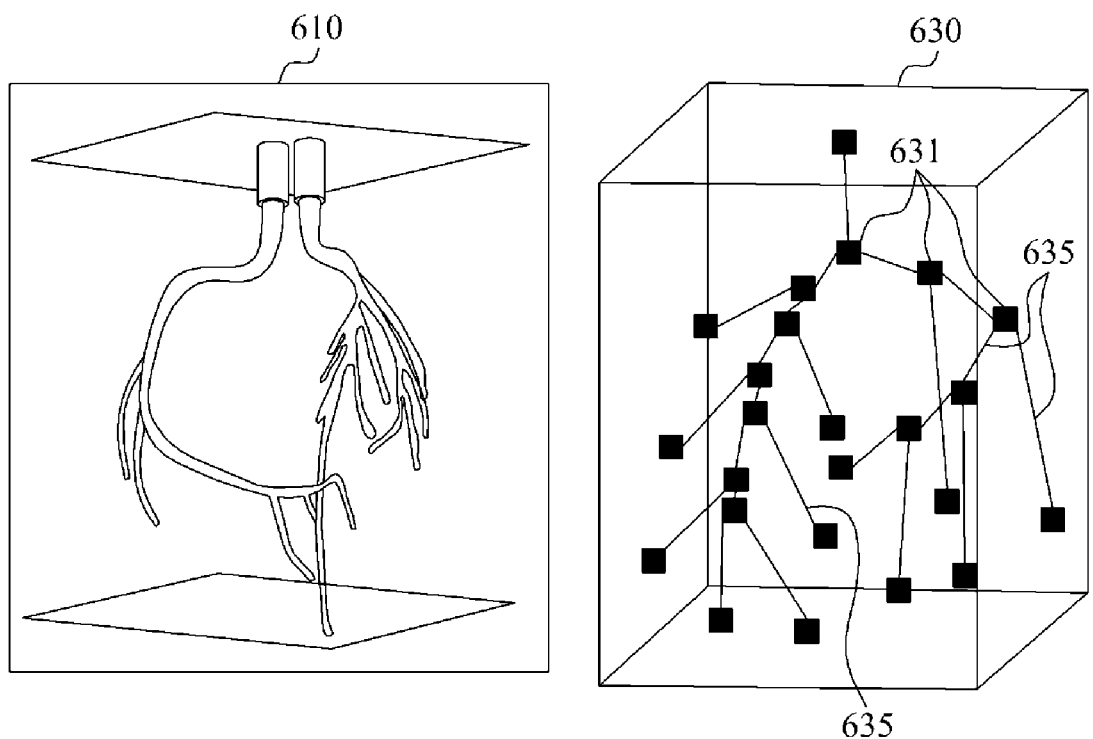
FIG. 6 is a diagram illustrating an example of a method of generating a blood vessel tree in a method of creating a model of a target organ.

FIG. 6 is a diagram illustrating an example of a method of generating a blood vessel tree 630 in a method of creating a model of a target organ. The blood vessel tree 630 is generated from a blood vessel structure 610 of the target organ. The blood vessel tree 630 includes branching points 631 and blood vessel lines 635.

For example, a method of thinning from a segmented image and a method of extracting a skeleton from marching cube surfaces may be performed to generate the blood vessel tree 630. The method of thinning from the segmented image includes thinning a thickness of a line figure in order to extract ideal line information. The method of extracting the skeleton from the marching cube surfaces includes extracting a 3D skeleton structure in order to analyze a shape of an object of which a phase structure is needed. The method of thinning from the segmented image method and the method of extracting the skeleton from the marching cube surfaces are technologies that are generalized in the art, and thus, a further detailed description will be omitted herein.

The blood vessel tree 630 may be generated for each phase of the target organ that is imaged. The blood vessel tree 630 generated for each phase may be configured to include the same topology. For example, a number of nodes or branching points 631, and the number of edges or blood vessel lines 635, that constitute the blood vessel tree 630, and their connectivity, may be configured to be identical for each phase.

For example, a number of nodes and a number of edges that constitute a blood vessel tree generated from an image captured during an inhalation may be identical to a number of nodes and a number of edges that constitute a blood vessel tree generated from an image captured during an exhalation. A vertex 0 in the blood vessel tree generated from the image captured during an inhalation may correspond to a vertex 0 in the blood vessel tree generated from the image captured during an exhalation. Also, a connection relationship in the blood vessel tree generated from the image captured during an inhalation (e.g., the vertex 0 is connected to vertices 1 and 3, and the vertices 1 and 3 are connected to a vertex 2) may be understood to be maintained as is in the blood vessel tree generated from the image captured during an exhalation.

Figure 7:
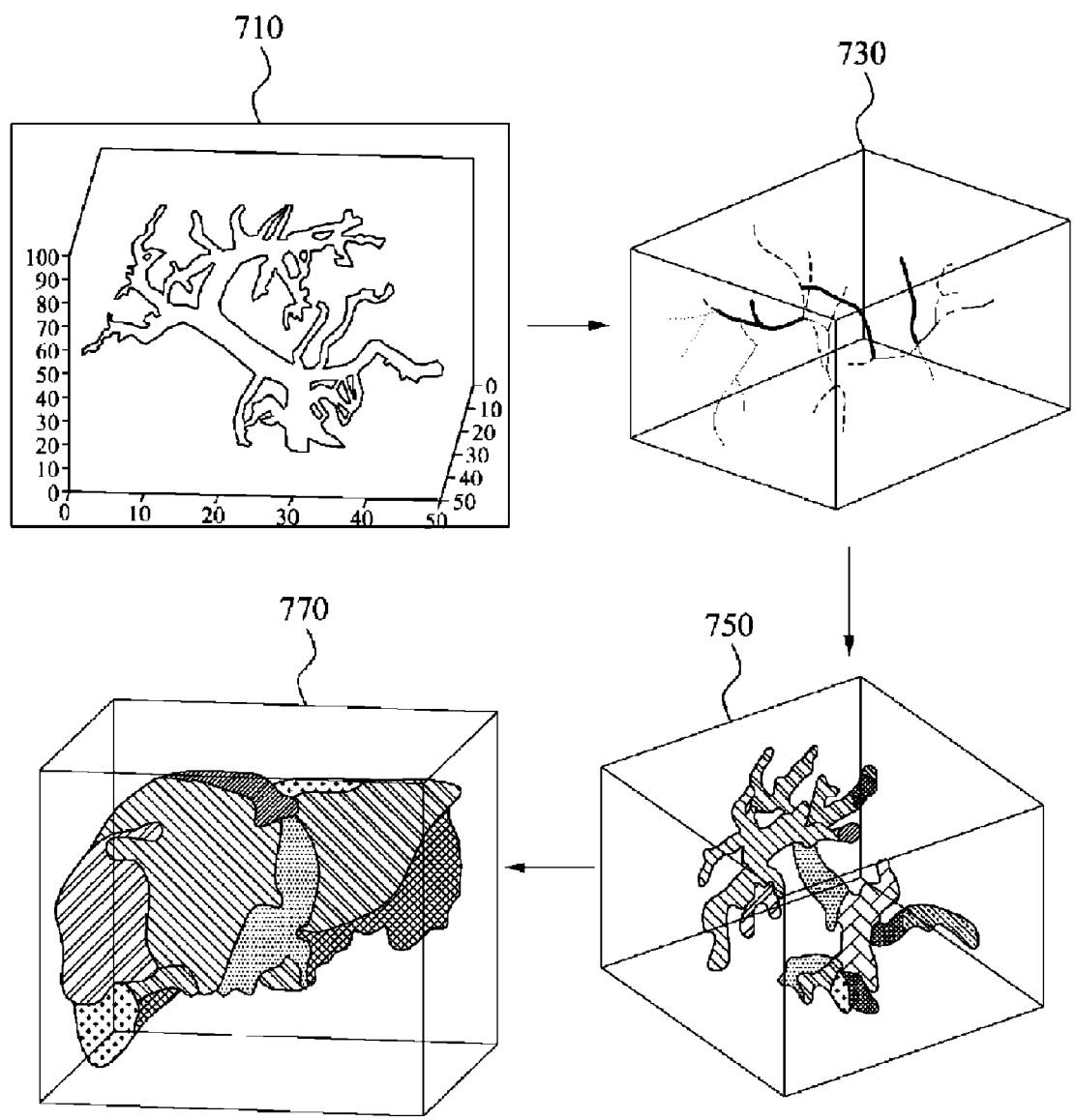
FIG. 7 is a diagram illustrating an example of a method of compartmentalizing an organ shape model of a target organ into areas in a method of creating a model of the target organ.

FIG. 7 is a diagram illustrating an example of a method of compartmentalizing an organ shape model of a target organ into areas in a method of creating a model of the target organ. Referring to FIG. 7, a creating apparatus segments a blood vessel structure in a 3D image of the target organ, and generates a blood vessel tree indicating the blood vessel structure. The creating apparatus further calculates an influence of each blood vessel line of the blood vessel tree with respect to a deformation of the organ shape model. The influence may be calculated based on a level of each user that uses the creating apparatus. The creating apparatus further compartmentalizes the organ shape model into areas based on the influence of each blood vessel line of the blood vessel tree with respect to the deformation of the organ shape model. For example, the creating apparatus may compartmentalize the organ shape model into the areas based on each blood vessel line including the largest influence with respect to a deformation of a corresponding area of the organ shape model, among blood vessel lines of the blood vessel tree. In another example, the compartmentalizing of the organ shape model into the areas may include pairing a blood vessel line of the blood vessel tree and an area of the organ shape model in which a deformation is greatly influenced by the corresponding blood vessel line.

In this example, the influence of each blood vessel line of the blood vessel tree with respect to the deformation of the organ shape model may be calculated based on a minimum distance function or a maximum potential function. An example of using the minimum distance function will be described with reference to FIG. 7.

In the example of using the minimum distance function, in operation 710, the creating apparatus segments the blood vessel structure in the 3D image of the target organ. In operation 730, the creating apparatus extracts a centerline from the blood vessel structure to generate a structure or a shape of the blood vessel tree. In operation 750, the creating apparatus calculates close points between branching points or the blood vessel lines of the blood vessel tree, and respective areas on a surface of the organ shape model, and distinguishably displays the respective blood vessel lines. In operation 770, the creating apparatus compartmentalizes the organ shape model into the areas that are most greatly influenced by (e.g., closest in distance to) corresponding blood vessel lines. For example, if a blood vessel line a is closest in distance to an area A on the surface of the organ shape model, the creating apparatus compartmentalizes the surface of the organ shape model to include the area A to be deformed along a motion of the blood vessel line a.

In the example of using the maximum potential function, the creating apparatus may give a different potential value for each branching point of the blood vessel tree, and then may spread the value. For example, if a potential value within a liver space is spread, and a relatively great potential function value is output in an area B of a liver, the area B and a branching point of the blood vessel tree may be paired.

Figure 8:
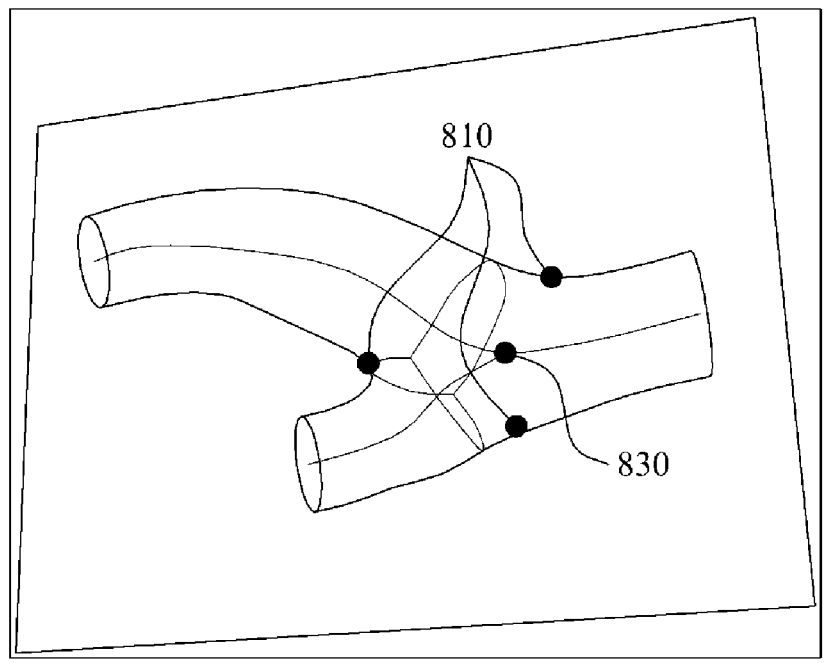
FIG. 8 is a diagram illustrating an example of a method of setting feature points in an organ shape model of a target organ in a method of creating a model of the target organ.

FIG. 8 is a diagram illustrating an example of a method of setting feature points in an organ shape model of a target organ in a method of creating a model of the target organ. The term "feature point" indicates a characteristic point or a vertex capable of distinguishing the target organ of a patient from an organ of another person, and may be classified as a feature point on a surface and a feature point of an internal structure. For example, the feature point on the surface may include a position of a wrinkle appearing between a left lobe and a right lobe of the target organ (e.g., liver), and a vertex at which a primary blood vessel or a nerve of the target organ passes. The feature point of the internal structure may include, for example, an extreme phase of a blood vessel positioned within the target organ, a branching point of the blood vessel, a high curvature point in the blood vessel, a surface of the blood vessel, and a position of a tumor within the target organ.

Referring to FIG. 8, feature points 810 are set at positions indicating high curvatures on an external surface of a blood vessel. A feature point 830 is set at a center point of branching points of the blood vessel.

Feature points set in an organ shape model may be used to match respective feature points extracted from a 2D run-time image, or may be used as constraints when extracting a feature point from the 2D run-time image, as described herein.

Figure 9:
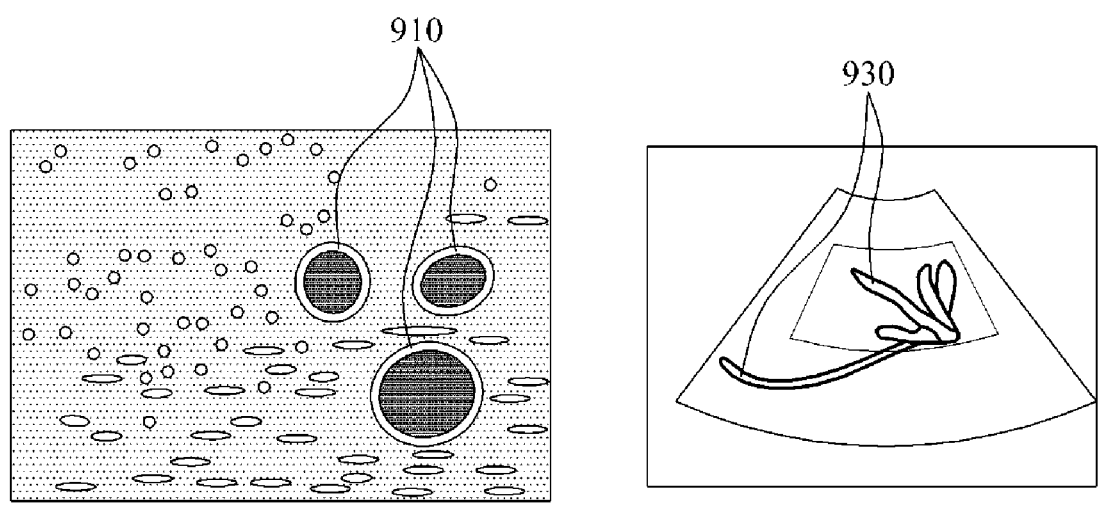
FIG. 9 is a diagram illustrating an example of a method of extracting feature points from a two-dimensional (2D) run-time image of a target organ in a method of creating a model of the target organ.

FIG. 9 is a diagram illustrating an example of a method of extracting feature points from a 2D run-time image of a target organ in a method of creating a model of the target organ. Referring to FIG. 9, feature points extracted from the 2D run-time image may be tumors 910 appearing in a 2D ultrasound image. In another example, feature points extracted from the 2D run-time image may be blood vessels or a blood vessel structure 930 that are distinguishable in a 2D ultrasound image.

To perform matching of first and second feature points as described above with operation 270 of FIG. 2, a feature point set in an organ shape model of a target organ and a feature point extracted from a run-time image of the target organ may include identical topology.

Figure 10:
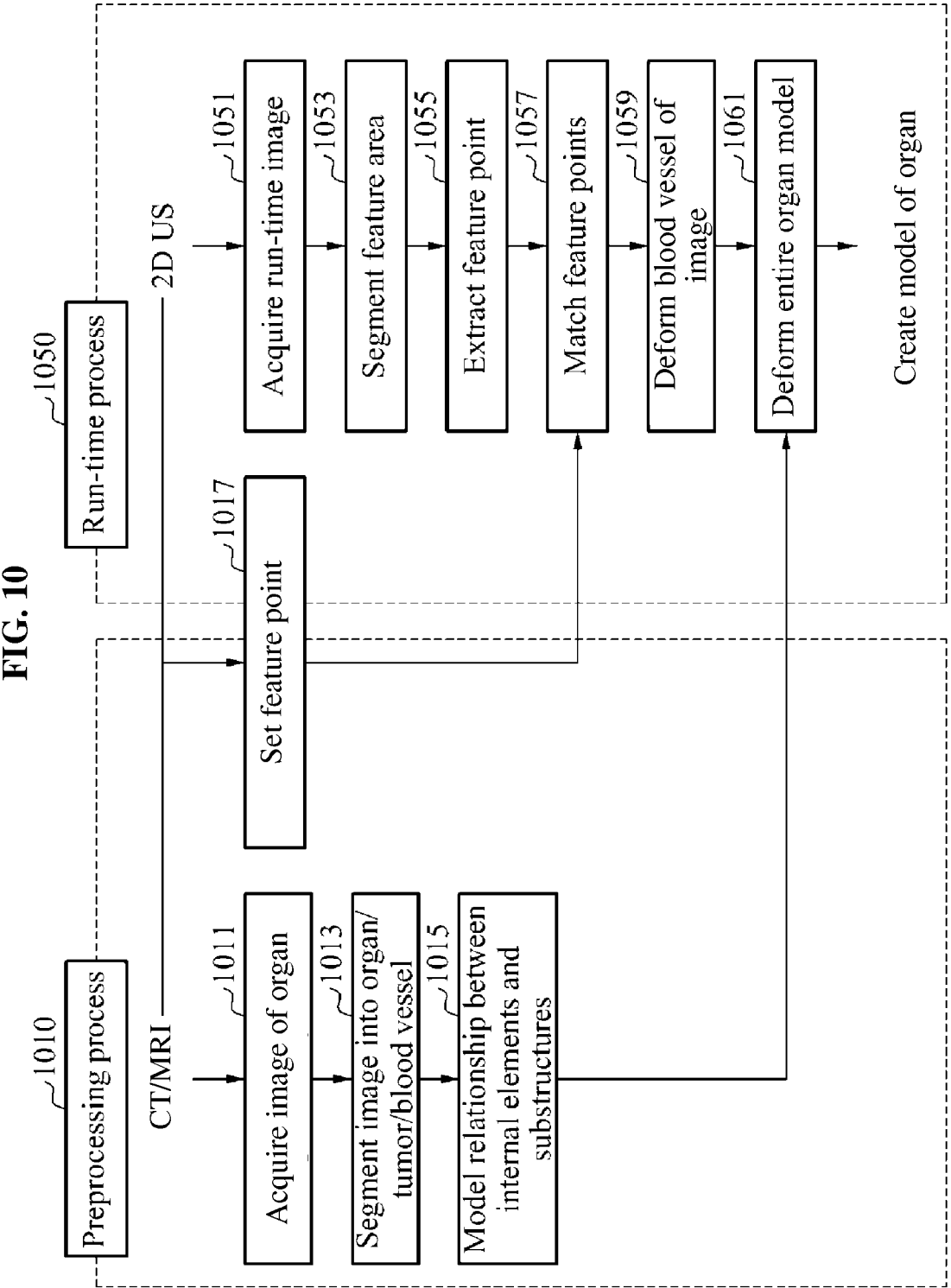
FIG. 10 is a flowchart illustrating still another example of a method of creating a model of a target organ.

FIG. 10 is a flowchart illustrating still another example of a method of creating a model of a target organ. Referring to FIG. 10, the method of creating the model of the target organ includes a preprocessing process 1010 preoperatively performed before a surgery, and a run-time process 1050 performed during run time and during the surgery.

During the preprocessing process 1010, in operation 1011, a creating apparatus acquires a 3D medical image, for example, a CT image or an MRI image, of the target organ specified for a patient.

In operation 1013, the creating apparatus segments the 3D medical image into elements, for example, the target organ, a tumor, and a blood vessel.

In operation 1015, the creating apparatus models a relationship between substructures and internal elements within the target organ, for example, a partial blood vessel, the entire blood vessel, and the tumor, to create an organ shape model. For example, the creating apparatus may create a shape of an internal element in which the target organ, the tumor, and the blood vessel are segmented, for each phase of the target organ that is imaged. The creating apparatus further generates a blood vessel tree of the organ shape model, and compartmentalizes the organ shape model into areas based on an influence of each blood vessel line of the blood vessel tree with respect to a deformation of the organ shape model.

In operation 1017, the creating apparatus set at least one first feature point in the 3D medical image to deform the entire organ shape model. For example, the feature point may correspond to the blood vessel.

During the run-time process 1050, in operation 1051, the creating apparatus acquires a run-time image, for example, a 2D US image photographed using an endoscope, of the target organ.

In operation 1053, the creating apparatus segments a feature area, for example, a thick blood vessel, of the run-time image.

In operation 1055, the creating apparatus extracts at least one second feature point from the run-time image.

In operation 1057, the creating apparatus matches the first feature point to the second feature point.

In operation 1059, the creating apparatus deforms the blood vessel of the 3D medical image to fit the blood vessel of the run-time image based on the matched first and second feature points In operation 1061, the creating apparatus deforms the entire organ shape model based on the deformed blood vessel structure. Accordingly, the creating apparatus creates the model of the target organ based on the deformed organ shape model and the areas of the organ shape model.

The examples of the creating apparatus described may generate a pre-operative internal structure of a target organ specified for a patient. The creating apparatus may further merge the pre-operative internal structure with feature points of a run-time medical image for the target organ that is captured during a surgery, which thereby deforms a shape of the pre-operative internal structure. For example, the preoperative internal structure may include a partial blood vessel, an entire blood vessel, a tumor, a blood vessel structure, and/or other elements known to one of ordinary skill in the art. The feature points of the run-time medical image may correspond to, for example, a thick blood vessel, a tumor, and/or other elements known to one of ordinary skill in the art. However, the examples are not limited thereto.

Accordingly, when creating a model of a patient-specified target organ, a sequential deformation method of segmenting a feature area, for example, a blood vessel and a tumor, of a run-time image of the target organ, and deforming a model of the target organ based on the feature area may be employed. Even though a captured shape of the target organ is incomplete, a substructure within the target organ may be modeled or classified by estimating a neighboring area based on, e.g., a vertex and/or an edge, of a deformation space in which organ shape models of respective phases for the target organ are defined, as illustrated in FIG. 5.

Figure 11:
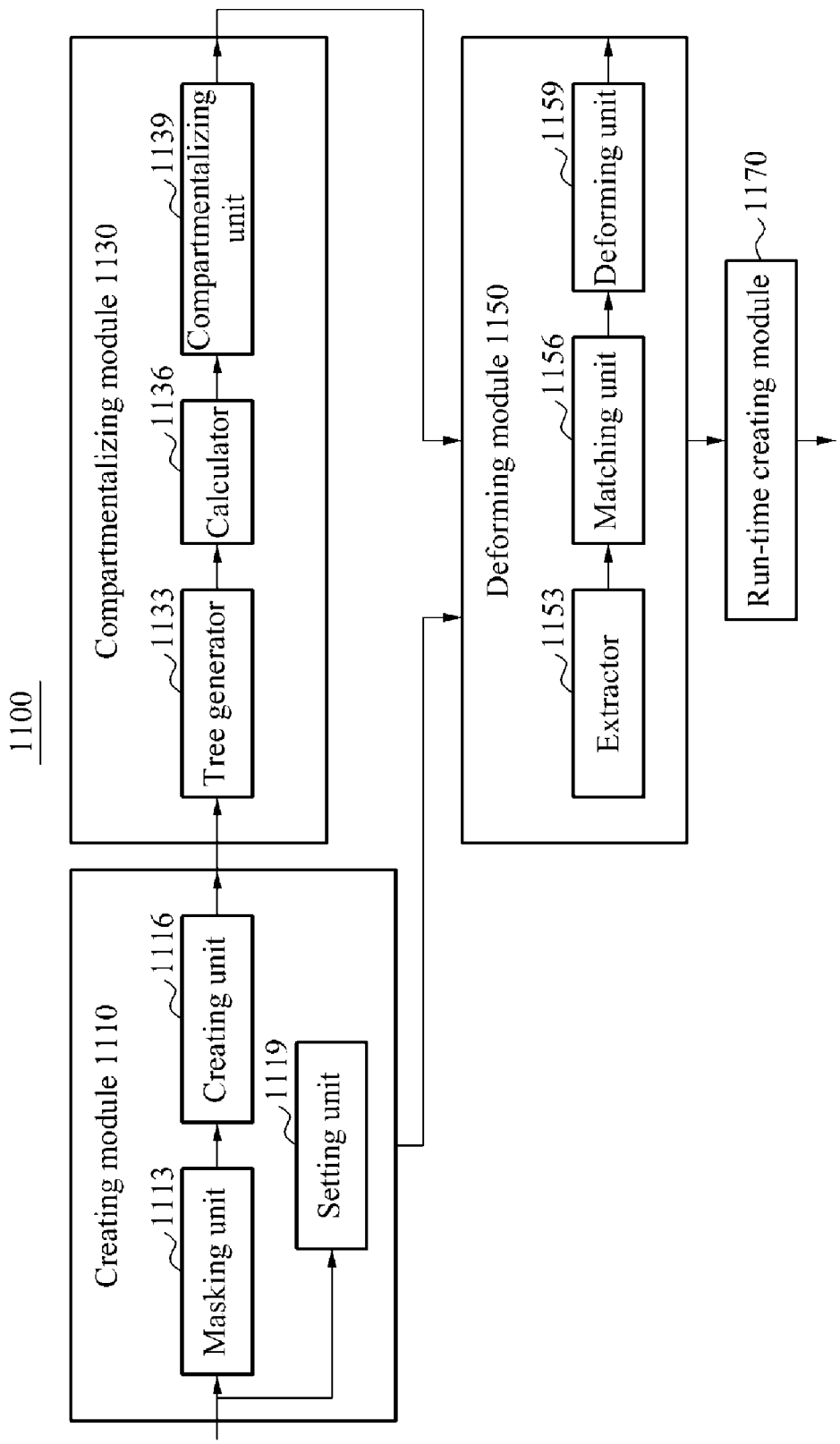
FIG. 11 is a block diagram illustrating an example of an apparatus that creates a model of a target organ.

FIG. 11 is a block diagram illustrating an example of an apparatus 1100 (hereinafter, a creating apparatus 1100) that creates a model of a target organ. Referring to FIG. 11, the creating apparatus 1100 includes a creating module 1110, a compartmentalizing module 1130, a deforming module 1150, and a run-time creating module 1170.

The creating module 1110 is configured to create an organ shape model, including a blood vessel structure, of the target organ specified for a patient based on at least two 3D images of respective phases for the target organ. The creating module 1110 includes a masking unit 1113, a creating unit 1116, and a setting unit 1119.

The masking unit 1113 is configured to mask an area, including the target organ, a blood vessel of the target organ, and/or a tumor, in each of the 3D images.

The creating unit 1116 is configured to create at least two organ shape models of the respective phases for the target organ based on the masked area in each of the 3D images. The creating unit 1116 may be further configured to select a reference shape model from among the organ shape models of the respective phases for the target organ, and to create the organ shape models of the respective phases for the target organ based on a deformation relationship between the reference shape model and each of remaining shape models. The creating unit 116 may be further configured to calculate the deformation relationship between the reference shape model and each of the remaining shape models based on a deformation gradient corresponding to each of the reference shape model and the remaining shape models.

The setting unit 1119 is configured to set one or more first feature points in the blood vessel structure of the organ shape model. The first feature points may be used to match one or more second feature points of a blood vessel structure for a 2D run-time image of the target organ, or may be used as constraints when extracting the second feature point from the 2D run-time image.

The compartmentalizing module 1130 is configured to compartmentalize the organ shape model into areas based on an influence of each blood vessel line of a blood vessel tree with respect to a deformation of the organ shape model. The blood vessel tree indicates the blood vessel structure of the target organ. The compartmentalizing module 1130 includes a tree generator 1133, a calculator 1136, and a compartmentalizing unit 1139.

The tree generator 1133 is configured to generate the blood vessel tree indicating the blood vessel structure of the target organ.

The calculator 1136 is configured to calculate an influence of each blood vessel line of the blood vessel tree with respect to a deformation of the organ shape model based on a minimum distance function or a maximum potential function.

The compartmentalizing unit 1139 is configured to compartmentalize the organ shape model into the areas based on the influence of each blood vessel line of the blood vessel tree with respect to the deformation of the organ shape model. For example, the compartmentalizing unit 1139 may be configured to compartmentalize the organ shape model into the areas based on each blood vessel line including the largest influence with respect to a deformation of a corresponding area of the organ shape model, among blood vessel lines of the blood vessel tree.

The deforming module 1150 is configured to deform the blood vessel structure of the organ shape model to fit the blood vessel structure of the 2D run-time image based on the first feature points matched to the second feature points. The deforming module 1150 includes an extractor 1153, a matching unit 1156, and a deforming unit 1159.

The extractor 1153 is configured to extract the second feature points from the blood vessel structure of the 2D run-time image.

The matching unit 1156 is configured to match the first feature points to the second feature points.

The deforming unit 1159 is configured to deform the blood vessel structure of the organ shape model to fit the blood vessel structure of the 2D run-time image based on the matched first and second feature points.

The run-time creating module 1170 is configured to create the model of the target organ during run time based on the deformed blood vessel structure and the areas of the organ shape model.

The various modules, units, and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may include various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions that control a processing device to implement a software component may include a computer program, a piece of code, an instruction, or some combination thereof, that independently or collectively instructs or configures the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments that implement the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer-implemented method of modelling an organ, the method comprising:
   obtaining a 3D shape model, corresponding to a patient, comprising a 3D blood vessel structure of the organ;
   obtaining an influence of a 3D blood vessel tree indicating the 3D blood vessel structure on a deformation of the 3D shape model, wherein the 3D shape model is compartmentalized into areas based on the influence;
   receiving a 2D image, corresponding to the patient, of the organ;
   extracting a 2D blood vessel structure from the 2D image;
   deforming the 3D blood vessel tree based on the 2D blood vessel structure; and
   generating a 3D patient-specified shape model fit to the 2D image by deforming the 3D shape model based on the deformed 3D blood vessel tree, the influence and the areas.

2. The method of claim 1, further comprising:
   calculating an influence of each blood vessel line of the 3D blood vessel tree, with respect to the deformation of the 3D shape model,
   wherein the compartmentalizing comprises compartmentalizing the 3D shape model into the areas, based on the influence of each blood vessel line.

3. The method of claim 2, wherein the calculation is based on a minimum distance function or a maximum potential function.

4. The method of claim 2, wherein the compartmentalizing comprises: compartmentalizing the 3D shape model into the areas, based on blood vessel lines having a largest influence with respect to a deformation of a corresponding area of the 3D shape model, among blood vessel lines of the 3D blood vessel tree.

5. The method of claim 1, further comprising:
setting first feature points in the 3D blood vessel structure; and
extracting second feature points from the 2D blood vessel structure,
wherein the deforming the 3D blood vessel tree comprises deforming the 3D blood vessel structure tree to fit the 2D blood vessel structure, based on the first and second feature points.

6. The method of claim 5, further comprising:
matching the first feature points to the second feature points,
wherein the deforming the 3D blood vessel tree comprises deforming the 3D blood vessel tree to fit the 2D blood vessel structure, based on the matched first and second feature points.

7. The method of claim 1, further comprising:
selecting a reference shape model from shape models,
wherein the obtaining the 3D shape model comprises creating the 3D shape
models, based on a deformation relationship between the reference shape model and remaining shape models.

8. The method of claim 7, further comprising:
calculating the deformation relationship between the reference shape model and the remaining shape models, based on a deformation gradient corresponding to each of the reference shape model and the remaining shape models.

9. The method of claim 1, further comprising:
masking an area, comprising a blood vessel of the organ and/or a tumor, in 3D images; and
creating shape models of respective phases of the organ, based on the masked area.

10. The method of claim 1, wherein the obtaining the 3D shape model comprises:
creating the 3D shape model, comprising the 3D blood vessel structure, based on three-dimensional (3D) images of the organ.

11. A non-transitory computer-readable storage medium storing a program comprising instructions to cause a computer to perform the method of claim 1.

12. An apparatus that performs modelling of an organ, the apparatus comprising:
a processor configured to:
obtain a 3D shape model, corresponding to a patient, comprising a 3D blood vessel structure of the organ;
obtain an influence of a 3D blood vessel tree indicating the 3D blood vessel structure on a deformation of the 3D shape model, wherein the 3D shape model is compartmentalized into areas based on the influence;
receive a 2D image, corresponding to the patient, of the organ;
extract a 2D blood vessel structure from the 2D image;
deform the 3D blood vessel tree, based on the 2D blood vessel structure; and
generate a 3D patient-specified shape model fit to the 2D image by deforming the 3D shape model based on the deformed 3D blood vessel tree, the influence and the areas.

13. The apparatus of claim 12, the processor further configured to:
calculate an influence of each blood vessel line of the 3D blood vessel tree, with respect to the deformation of the 3D shape model; and
compartmentalize the 3D shape model into areas, based on the influence of each blood vessel line.

14. The apparatus of claim 13, wherein the calculation is based on a minimum distance function or a maximum potential function.

15. The apparatus of claim 13, wherein the processor is further configured to:
compartmentalize the 3D shape model into the areas, based on blood vessel lines having a largest influence with respect to a deformation of a corresponding area of the 3D shape model, among blood vessel lines of the 3D blood vessel tree.

16. The apparatus of claim 12, wherein the processor is further configured to:
deform the 3D blood vessel tree to fit the 2D blood vessel structure, based on first feature points set in the 3D blood vessel structure, and second feature points extracted from the 2D blood vessel structure.

17. The apparatus of claim 12, wherein the processor is further configured to:
set first feature points in the 3D blood vessel structure; and
extract second feature points from the 2D blood vessel structure,
wherein the processor is further configured to deform the 3D blood vessel tree to fit the 2D blood vessel structure, based on the first and second feature points.

18. The apparatus of claim 17, wherein the processor is further configured to:
match the first feature points to the second feature points; and
deform the 3D blood vessel tree to fit the 2D blood vessel structure, based on the matched first and second feature points.

19. The apparatus of claim 12, wherein the processor is further configured to:
select a reference shape model from shape models; and
create the 3D shape models, based on a deformation relationship between the
reference shape model and remaining shape models.

20. The apparatus of claim 19, wherein the processor is further configured to:
calculate the deformation relationship between the reference shape model and the remaining shape models, based on a deformation gradient corresponding to each of the reference shape model and the remaining shape models.

21. The apparatus of claim 12, wherein the processor is further configured to:
mask an area, comprising a blood vessel of the organ and/or a tumor, in 3D images; and
create shape models of respective phases of the organ, based on the masked area.

* * * * *